United States Patent [19]
Platzek et al.

[11] Patent Number: 6,114,321
[45] Date of Patent: Sep. 5, 2000

[54] PORPHYRIN DERIVATIVES, PHARMACEUTICAL AGENTS THAT CONTAIN THE LATTER, AND THEIR USE IN PHOTODYNAMIC THERAPY AND MRI DIAGNOSIS

[75] Inventors: Johannes Platzek; Ulrich Niedballa; Bernd Raduechel; Hanns-Joachim Weinmann; Thomas Frenzel, all of Berlin; Wolfgang Ebert, Mahlow, all of Germany

[73] Assignee: Schering Aktiengesellschaft, Berlin, Germany

[21] Appl. No.: 09/346,891

[22] Filed: Jul. 2, 1999

Related U.S. Application Data

[60] Provisional application No. 60/110,696, Dec. 3, 1998.

[30] Foreign Application Priority Data

Jul. 3, 1998 [DE] Germany .......................... 198 31 217

[51] Int. Cl.[7] .......................... C07D 487/22; A61K 31/40
[52] U.S. Cl. .......................... 514/185; 514/183; 514/184; 514/186; 540/145; 540/472; 540/474; 540/465; 424/9.362; 534/15

[58] Field of Search ...................... 514/185, 183, 514/184, 186; 540/145, 474; 424/9.362; 534/15

[56] References Cited

U.S. PATENT DOCUMENTS

| | | | |
|---|---|---|---|
| 5,053,503 | 10/1991 | Dean et al. | 540/474 |
| 5,252,720 | 10/1993 | Sessler et al. | 534/11 |
| 5,457,183 | 10/1995 | Sessler et al. | 534/11 |
| 5,504,205 | 4/1996 | Sessler et al. . | |
| 5,559,207 | 9/1996 | Sessler et al. | 530/300 |
| 5,599,923 | 2/1997 | Sessler et al. | 540/145 |

OTHER PUBLICATIONS

International Search Report for PCT/EP99/04150 mailed Oct. 11, 1999.

*Primary Examiner*—Mukund J. Shah
*Assistant Examiner*—Pavanaram K Sripada
*Attorney, Agent, or Firm*—Millen, White, Zelano & Branigan P.C.

[57] ABSTRACT

The invention relates to new porphyrin complex compounds, pharmaceutical agents that contain the latter, and the use of porphyrin complexes for the production of agents for photodynamic therapy and MRI diagnosis.

21 Claims, No Drawings

PORPHYRIN DERIVATIVES, PHARMACEUTICAL AGENTS THAT CONTAIN THE LATTER, AND THEIR USE IN PHOTODYNAMIC THERAPY AND MRI DIAGNOSIS

The instant application claims benifit of U.S. Provisional Application Serial No. 60/110,696, filed Dec. 3, 1998.

DESCRIPTION

The invention relates to the subjects that are characterized in the claims, i.e., new porphyrin-complex compounds, pharmaceutical agents that contain the latter, and the use of porphyrin complexes for the production of agents for photodynamic therapy and MRI diagnosis.

A promising process for the treatment of diseases, especially of tumors in tissues that are close to the surface or in hollow organs (bladder, esophagus), is photodynamic therapy (PDT). In this technique, a photosensitizing dye is used that accumulates in the tumor. Said dye is then irradiated, so that oxygen is converted into the highly reactive form of singlet-oxygen$^1$ $O_2$ under the action of the dye. This oxygen form is cytotoxic and kills the tissue (preferably tumor tissue) in its surrounding area.

Porphyrins also belong to the families of substances that are suitable for PDT. They accumulate in tumors and absorb light in a range in which living tissue is still fairly permeable, namely between 700–900 nm. Moreover, porphyrins exhibit yet other properties that are valuable for PDT: high yields in the excited triplet state, a long life of this state, and a good energy transfer to the oxygen with the formation of $^1O_2$.

Of the porphyrins (WO 92/06097, WO 97/20846; EP 0 811626; U.S. Pat. No. 5,633,275, U.S. Pat. No. 5,654,423, U.S. Pat. No. 5,675,001, U.S. Pat. No. 5,703,230, U.S. Pat. No. 5,705,622) and their derivatives, photofrin II (U.S. Pat. No. 4,882,234) is already on the market; others are in turn undergoing clinical trials. Photofrin II is a mixture of oligomers of hematoporphyrin, whereby ester and ether bonds connect the subunits to one another.

BPDMA (verteporphin, WO 97/48393), a benzoporphyrin derivative, is in clinical phase II. This compound is used to combat cancer of the skin and psoriasis and is especially successful in the case of age-related macular degeneration (AMD), a disease that can lead to blindness.

For the treatment of esophageal or bronchial carcinomas, mTHPC (WO 95/29915) is being studied. MACE, a monoaspartyl-chlorine (CA 2121716; JP 09071531), also belongs to the group of chlorines. The patent literature mentions a group of chlorines that are suitable for PDT (see WO 97/19081, WO 97/32885; EP 0 569113; U.S. Pat. No. 5,587,394, U.S. Pat. No. 5,648,485, U.S. Pat. No. 5,693,632).

In addition to the above-mentioned compounds, porphyrin-like unsaturated systems such as porphyrin-isomeric porphycene (WO 92/12636, WO 93/00087, WO 96/31451, WO 96/31452; U.S. Pat. No. 5,610,175, U.S. Pat. No. 5,637,608) and phtalocyanines (U.S. Pat. No. 5,686,439), texaphyrins (WO 95/10307; U.S. Pat. No. 5,591,422, U.S. Pat. No. 5,594,136, U.S. Pat. No. 5,599,923, U.S. Pat. No. 5,599,928, U.S. Pat. No. 5,622,946), and purpurins are now also being studied. The common structural feature of the three last-mentioned classes is that they are metal derivatives. The absorption band in the long-wave range is frequently shifted by the metalization.

Paramagnetic metal ions have a negative effect on the life of the triplet state. The shortening of the life of this stage can exceed a factor of $10^3$. The triplet state is responsible for the energy transfer to the oxygen, but if the life is too short, singlet oxygen can no longer be formed.

Diamagnetic metal ions, however, stabilize the triplet state and thus increase the quantum yield of $^1O_2$. Zinc, tin, cadmium, aluminum, lutetium, indium, and yttrium are thus found as central ions in photosensitizing π-systems.

Zn-phthalocyanine is being studied as an active ingredient to combat age-related macular degeneration (AMD). A sulfonated phthalocyanine is being tested as an aluminum derivative to determine its action (photosense, Russia).

Tin-ethiopurpurin (WO 96/32094) is being studied with regard to its action against Kaposi's sarcoma, however.

As a representative of the expanded porphyrins, Lu-texaphyrin must be mentioned. The compound has a very long-lived triplet state and yields singlet oxygen in quantum yields of over 70%. It is being tested to determine its usability as an agent in the treatment of restenosis and is already in clinical phase I.

With the expanded porphyrins, rubyrins (U.S. Pat. No. 5,622,945), sapphyrins (U.S. Pat. No. 5,457,195), and porphyrazins (U.S. Pat. No. 5,675,001) can also be mentioned, which are also suitable for PDT owing to their absorption at 620–690 nm.

A very extensive description of chemical synthesis and properties with respect to suitability for photodynamic therapy is found in Chem. Rev. 1997, 97, 2267–2340, A. Jasat and D. Dolphin, Expanded Porphyrins and their Heterologs.

As already mentioned, the toxic action of the photosensitizer manifests itself where active ingredient and light collide. This means that concentration or longer retention in the skin results in an undesirable photosensitization of the skin. The duration of sensitization ranges from several days (MACE, BPDMA~3 days) to several weeks (m-THPC~3 weeks) to a month (photofrin II~30 days). In this time, exposure to light must be carefully avoided.

A significant drawback of the above-mentioned compounds that were previously used for PDT is that they are suitable only for therapy; simultaneous MRI-diagnostic monitoring of the success of the therapy is not possible with them. For this purpose, it is necessary to administer another paramagnetic substance which, moreover, must have a biodistribution that is as close to that of the therapeutic agent as possible. This requirement often cannot be met.

There is therefore a need for MRI-diagnostic agents for therapy monitoring of PDT. Compounds that are suitable both for PDT and for MRI-diagnostic therapy monitoring would be ideal.

It has been found, surprisingly enough, that porphyrin complexes consist of a ligand of general formula I

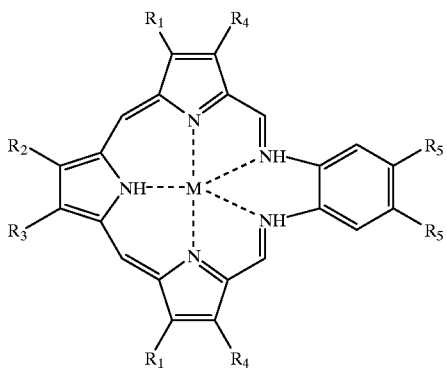

(I)

and at least one ion of an element of atomic numbers 20–32, 37–39, 42–51, or 57–83, in which M stands for a diamagnetic metal, $R^1$, $R^2$, $R^3$ and $R^4$, independently of one another, mean a hydrogen atom or a $C_1$–$C_{30}$ alkyl radical, which optionally is interrupted by 1–10 oxygen atoms and/or optionally is substituted with 1–5 hydroxy groups or 1–2 COOH groups, $R^5$ represents a radical —$(O)_{0,1}$—L—NH—K, in which L means a linker chain that consists of a straight-chain or branched $C_1$–$C_{20}$ alkyl radical, which optionally is interrupted by 1–8 oxygen atoms, 1–5 NH groups, 1–5 CO groups, 1–5 NHCO groups, 1–5 CONH groups, or 1–3 sulfur atoms, or L stands for 1–2 phenylene groups, and K stands for a completing agent of general formula (IIa), (IIb), (IIc) or (IId),

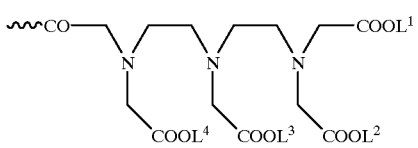

(IIa)

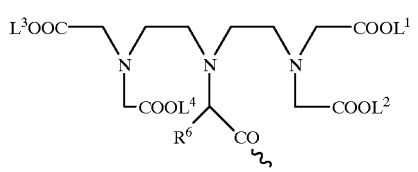

(IIb)

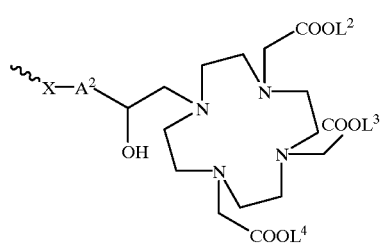

(IIc)

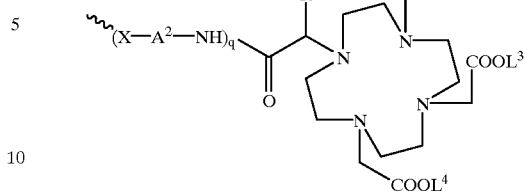

(IId)

in which q means number 0 or 1, $A^2$ stands for a phenylene group, a —$CH_2$—NHCO—$CH_2$—CH($CH_2$COOH)—$C_6H_4$ group, a phenylenoxy group, or a $C_1$–$C_{12}$ or $C_7$–$C_{12}$ alkylene group that is optionally interrupted by one or more oxygen atoms, 1 to 3 —NHCO groups, 1 to 3 —CONH groups and/or substituted with 1 to 3 —$(CH_2)_{0-5}$ COOH groups, X means a —CO group or an —NHCS group, $R^6$ stands for a hydrogen atom, a straight-chain or branched $C_1$–$C_7$ alkyl group, a phenyl or benzyl group, and $L^1$, $L^2$, $L^3$ and $L^4$, independently of one another, stand for a hydrogen atom or a metal ion equivalent of an element of the above-mentioned atomic number, provided that at least two of these substituents stand for metal ion equivalents and that other anions are present to compensate for optionally present charges in the metalloporphyrin, and in which free carboxylic acid groups that are not required for complexing can also be present as salts with physiologically compatible inorganic and/or organic cations or as esters or as amides.

The compounds of general formula I contain paramagnetic ions and are suitable for use in MRI diagnosis.

It is surprising, however, that despite the presence of these ions in the molecule, the quantum yield in the triplet state is so high that adequate singlet-oxygen is produced to operate successful PDT. According to the generally accepted wording of "long distance—electron/energy transfer" processes (Photoprocesses in Transition Metal Complexes, Biosystems and Other Molecules: Experiment and Theory, Publisher Elise Kochanski, Kluwer Academic Publishers, NATO DSI Series, p. 375; Photoinduced Electron Transfer, Vol. 1–4, Publisher M. A. Fox, M. Charon, Elsevir, New York 1988; M. D. Ward, Chem. Soc. Rev. 1997, 26, 365: T. Hayshi and H. Ogoshi, Chem. Soc. Rev. 1997, 26, 355; H. Dugas, Bioinorganic Chemistry, Springer Verlag, New York 1989; P. Tecilla et al., J. Am. Chem. Soc. 1990, 112, 9408; Y. Aoyama et al., J. Am. Chem. Soc. 1991, 113, 6233), a severe disruption of the triplet state—a drastic shortening of its life—would have been expected; and particularly the latter since it is known that interaction of photoactive centers in the molecules with donor or acceptor sites themselves takes place via hydrogen bridges, while even covalent bonds are present in the compounds of general formula I.

As other advantages of the compounds of general formula I, a) Good compatibility
b) very good water solubility
c) high effectiveness in PDT
d) good chemical stability in aqueous solution
e) short half-life in the body
f) complete excretion from the body
g) high relaxivity can be cited.

For use of the agents according to the invention in NMR diagnosis, paramagnetic metal ions must be present in the complex. These are especially divalent and trivalent ions of the elements of atomic numbers 21–29, 42, 44 and 57–70. Suitable ions are, for example, chromium(III), manganese (II), manganese(III), iron(III), cobalt(II), cobalt(III), nickel (II), copper(II), praseodymium(II), neodymium(III), samarium(III) and ytterbium(III) ions. Because of their high magnetic moment, the gadolinium(III), dysprosium(III), manganese(II) and iron(III) ions are especially preferred. M preferably stands for $Zn^{2+}$, $Sn^{2+}$, $Sn^{4+}$, $Cd^{2+}$, $Mg^{2+}$, $Al^{3+}$, $Lu^{3+}$, $La^{3+}$, $In^{3+}$, $B^{3+}$ and $Ga^{3+}$, especially preferably for $Lu^{3+}$ and $Zn^{2+}$.

The complexes according to the invention show, surprisingly enough, a considerably higher relaxivity compared to the structurally similar compounds that are known to date. Since the relaxivity can be regarded as a yardstick for the contrast medium action of a compound, a comparable, positive signal effect is possible even at a low dose with use of the complexes according to the invention in the area of NMR diagnosis. This significantly increases the safety margin, for which the product of relaxivity and compatibility can be considered as a guide value.

If an ion that is bonded in the porphyrin is present in a higher oxidation stage than +2, the excess charge(s) are compensated for by, e.g., anions of organic or inorganic acids, preferably by acetate, chloride, sulfate, nitrate, tartrate, succinate and maleate ions or by negative charge(s) that are present in $R^2$ and/or $R^3$.

The carboxyl groups that are not required for complexing of metal ions can optionally be present as esters, as amides or as salts of inorganic or organic bases. Suitable ester radicals are those with 1 to 6 C atoms, preferably ethyl esters; suitable inorganic cations are, for example, the lithium and the potassium ion, and especially the sodium ion. Suitable cations of organic bases are those of primary, secondary or tertiary amines, such as, for example, ethanolamine, diethanolamine, morpholine, glucamine, N,N-dimethylglucamine, especially meglumine.

Radical $R^1$ preferably means —$CH_2CH_2CH_2OH$ or —$CH_2CH_2OH$. In a preferred embodiment, radicals $R^2$ or $R^3$ mean the ethyl group. In another preferred embodiment, $R^2$ and $R^3$ stand for the same radical.

$A^2$ preferably stands for a —$CH_2$—, —$(CH_2)_2$—, —$CH_2OC_6H_4$-β, —$CH_2OCH_2$— —$C_6H_4$—, —$CH_2$—NHCO—$CH_2$—$CH(CH_2COOH)$—$C_6H_4$-β, whereby β stands for the binding site to X.

X preferably stands for the CO group.

$R^6$ preferably stands for a hydrogen atom or a methyl group.

As complexing agent radical K, preferably derivatives of diethylenetriaminepentaacetic acid and 1,4,7,10-tetraazacyclododecane-1,4,7-triacetic acid, which are bonded via a linker to the respective porphyrin, can be mentioned.

The production of the complex compounds of general formula I is carried out according to methods that are known in the literature (see, e.g., DE 4232925 for IIa; see, e.g., DE 19507822, DE 19580858 and DE 19507819 for IIb; see, e.g., U.S. Pat. No. 5,053,503, WO 96/02669, WO 96/01655, EP 0430863, EP 255471, U.S. Pat. No. 5,277,895, EP 0232751, U.S. Pat. No. 4,885,363 for IIc and IId).

The 1,2-dihydroxy-4,5-dinitrobenzene or the 3,3'-(4,5-dinitrobenzene-1,2-diyldioxy)-dipropanoyl chloride that are used as starting compounds are produced as described in U.S. Pat. No. 5,504,205. The production of 2,5-bis[(5-formyl-3-hydroxypyrrole-4-methylpyrrol-2-yl)-methyl]-3,4-diethylpyrrole can also be found in U.S. Pat. No. 5504205.

The introduction of the desired metals (e.g., Zn) into the porphyrins is carried out according to methods that are known in the literature (e.g., The Porphyrins, ed. D. Dolphin, Academic Press, New York 1980, Vol. V, p. 459; DE 4232925), whereby essentially the following can be mentioned:

a) The substitution of pyrrolic NH's (by heating the metal-free ligand with the corresponding metal salt, preferably acetate, optionally with the addition of acid-buffering agents, such as e.g., sodium acetate, in a polar solvent) or b) the "recomplexing," in which a metal that is already complexed by a ligand is displaced by the desired metal.

As solvents, mainly polar solvents, such as, e.g., methanol, glacial acetic acid, dimethylformamide, chloroform and water are suitable.

The introduction of diamagnetic metal M into the porphyrin system can be carried out before or after linkage of completing agent radical K. As a result, an especially flexible procedure for the synthesis of the compounds according to the invention is made possible.

The chelation of radical K is carried out in a way that is known in the literature (see, e.g., DE 34 01 052) by the metal oxide or metal salt (e.g., the nitrate, acetate, carbonate, chloride or sulfate) of the metal that is desired in each case being suspended or dissolved in polar solvents such as water or aqueous alcohols and being reacted with the corresponding amount of the complexing ligand. If desired, acidic hydrogen atoms or acid groups that are present can be substituted by cations of inorganic and/or organic bases or amino acids.

In this case, the neutralization is carried out with the aid of inorganic bases, such as, e.g., alkali or alkaline-earth hydroxides, -carbonates or -bicarbonates and/or organic bases such as, i.a., primary, secondary and tertiary amines, such as, e.g., ethanolamine, morpholine, glucamine, N-methyl- and N,N-dimethylglucamine, as well as basic amino acids, such as, e.g., lysine, arginine and ornithine or amides of originally neutral or acidic amino acids.

For the production of neutral complex compounds, enough of the desired bases can be added to, for example, the acidic complex salts in aqueous solution or suspension to ensure that the neutral point is reached. The solution that is obtained can then be evaporated to the dry state in a vacuum. It is commonly advantageous to precipitate the neutral salts that are formed by adding water-miscible solvents, such as, for example, lower alcohols (e.g., methanol, ethanol, isopropanol), lower ketones (e.g., acetone), polar ethers (e.g., tetrahydrofuran, dioxane, 1,2-dimethoxyethane) and thus to obtain easily isolated and readily purified crystallizates. It has proven especially advantageous to add the desired base as early as during the complexing of the reaction mixture and thus to eliminate a process step.

If the acidic complex compounds contain several free acid groups, it is often suitable to produce neutral mixed salts that contain both inorganic and organic cations as counterions.

This can happen, for example, by the complexing ligands being reacted in aqueous suspension or solution with the oxide or salt of the element that yields the central ion and half of the amount of an organic base that is required for neutralization, the complex salt that is formed being isolated, optionally purified and then mixed for complete neutralization with the required amount of inorganic base. The sequence in which the base is added can also be reversed.

Another way of obtaining neutral complex compounds consists in converting the remaining acid groups in the complex completely or partially into esters. This can happen by subsequent reaction on the finished complex (e.g., by exhaustive reaction of free carboxy groups with dimethylsulfate).

The production of the pharmaceutical agents according to the invention is also carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, e.g., tromethamine), small additions of complexing agents (such as, e.g., diethylenetriaminepentaacetic acid) or, if necessary, electrolytes such as, e.g., sodium chloride or, if necessary, antioxidants such as, e.g., ascorbic acid.

If suspensions or solutions of the agents according to the invention in water or in physiological salt solution are desired for enteral administration or other purposes, they are mixed with one or more adjuvant(s) that are commonly used in galenicals (e.g., methylcellulose, lactose, mannitol) and/or surfactant(s) (e.g., lecithins, Tween®, Myrj®) and/or flavoring substances for taste correction (e.g., ethereal oils).

In principle, it is also possible to produce the pharmaceutical agents according to the invention even without isolating the complex salts. In any case, special care must be taken to perform the chelation such that the salts and salt solutions according to the invention are virtually free of noncomplexed metal ions that have a toxic effect.

This can be ensured, for example, with the aid of color indicators such as xylenol orange by control titrations during the production process. The invention therefore also relates to the process for the production of complex compounds and their salts. As a final precaution, there remains purification of the isolated complex salt.

To avoid undesirable photoreactions of porphyrins, the compounds and agents according to the invention should be stored and handled as much as possible in a light-free environment.

The pharmaceutical agents according to the invention preferably contain 20 μmol/L to 200 mmol/L of the complex salt and are generally dosed in amounts of 0.01 μmol to 2 mmol/kg of body weight, both in their use for PDT and for therapy monitoring using MRI diagnosis. They are intended for enteral and parenteral administration or are administered with the methods of interventional radiology.

The agents according to the invention meet the varied requirements for suitability as agents for PDT and MRI contrast media. After administration, they are extremely well suited for enhancing the informational value of the image that is obtained with the aid of a nuclear spin tomograph by increasing the signal intensity. They also show the great effectiveness that is necessary to burden the body with the smallest possible amounts of foreign substances and the good compatibility that is necessary to maintain the noninvasive nature of the studies.

The good water-solubility of the agents according to the invention allows the production of highly concentrated solutions, so as to keep the volume burden of the circulation within justifiable limits and to compensate for the dilution by bodily fluid. In addition, the agents according to the invention show not only a high stability in vitro but also a surprisingly high stability in vivo, so that a release or an exchange of the ions, which are inherently toxic and not covalently bonded in the complexes, can be disregarded within the time that it takes for the contrast media to be completely excreted.

The invention is explained by the following examples.

EXAMPLE 1 a) Di-t-butyl-N,N'-[(4,5-dinitrobenzene-1,2-diyl)-dioxy]-bis [({[(1-oxo-propane-3,1-diyl)-imino]-ethane-2,1-diyl}-oxy)-ethane-2,1-diyl-dicarbamate 13.34 g (3.5 mmol) of 3,3'-(4,5-dinitro-benzene-1,2-diyldioxy)-dipropanoyl chloride, produced from dicarboxylic acid with thionyl chloride/pyridine as described in U.S. Pat. No. 5,504,205, is dissolved in 50 ml of dry dichloromethane and reacted with the mixture of 1.440 g (7.05 mmol) of N-[2-(aminoethoxy)-ethyl]-carbamic acid-t-butyl ester, produced according to U.S. Pat. No. 5,053,503, and 558 mg (7.05 mol) of dry pyridine in 25 ml of dry dichloromethane while being stirred. It is allowed to stir for one more hour, washed with 1N hydrochloric acid, sodium bicarbonate solution, and the solution is dried on sodium sulfate. Then, it is evaporated to the dry state in a vacuum, and the residue is purified by chromatography on silica gel. As an eluant, mixtures of hexane/ethyl acetate of increasing polarity are used. The product-containing fractions are combined and concentrated by evaporation. 2.19 g (87.2% of theory) of the title compound is obtained.

Elementary analysis:

| Cld: | C 50.27 | H 6.75 | N 11.73 |
| --- | --- | --- | --- |
| Fnd: | C 50.41 | H 6.82 | N 11.66 | b) Di-t-butyl-N,N'-[(4,5-diaminobenzene-1,2-diyl)-dioxy]-bis[({(1-oxo-propane-3,1-diyl)-imino]-ethane-2,1-diyl}-oxy)-ethane-2,1-diyl-dicarbamate 2.150 g (3 mmol) of the dinitro compound that is produced under Example 1a) is added to 50 ml of dry ethanol. It is mixed with 100 mg of 10% Pd/C and refluxed. Then, 1.47 ml (30.1 mmol) of hydrazine hydrate is added in drops to 5 ml of dry ethanol while being stirred. The heating is continued until the dark solution becomes considerably lighter. The study of a thin-layer sample indicates that a more polar product has formed. It is hot-filtered through a layer of diatomaceous earth, rewashed with hot, dry ethanol, and evaporated to the dry state. The title compound is obtained as a light powder.

Yield: 1.854 g (94.1% of theory)

Elementary analysis:

| Cld: | C 54.86 | H 7.98 | N 12.80 |
| --- | --- | --- | --- |
| Fnd: | C 54.92 | H 8.06 | N 12.72 | c) Di-t-butyl-N,N'-{[9,10-diethyl-5,14-bis(3-hydroxypropyl)-4,15-dimethyl-3,6;8,1]: 13,16-triimino-1,18-benzodiazacyclo-eicosane-20,21-diyl)-bis[({[oxy-(1-oxo-propane-3,1-diyl)-imino]-ethane-2,1-diyl}-oxy)-ethane-2,1-diyl]}-dicarbamate 722.4 mg (1.5 mmol) of the 2,5-bis[(5-formyl-3-hydroxypyrrole-4-methylpyrrol-2-yl)-methyl]-3,4-diethylpyrrole that is produced according to U.S. Pat. No. 5,504,205 and 985.2 mg (1.5 mmol) of the diamine that is produced under Example 1b) are dissolved while being heated in a mixture of 1.6 l of oxygen-pure dry benzene that is flushed with argon and 200 ml of dry methanol. Then, 50 ml of dry methanol, in which 0.3 ml of concentrated hydrochloric acid is dissolved, is added, and it is refluxed under argon cover gas for 24 hours. It is allowed to cool, neutralized by adding 120 mg of powdered potassium carbonate and filtered by magnesium sulfate. It is evaporated to the dry state, taken up in dichloromethane and purified by chromatography on silica gel. The title compound is eluted with mixtures of hexane/ethyl acetate.

Yield: 1.402 g (84.8% of theory)

Elementary analysis:

| Cld: | C 63.19 | H 7.95 | N 11.44 |
|---|---|---|---|
| Fnd: | C 63.27 | H 8.01 | N 11.50 | d) $Lu^{3+}$ Complex of di-t-butyl-N,N'-{[(9,10-diethyl-5,14-bis(3-hydroxypropyl)-4,15-dimethyl-8,11-imino-3,6: 13,16 dinitrilo-1,18-benzodiazacyclo-eicosine-20,21-diyl]-bis[({[oxy-(1-oxo-propane-3,1-diyl)-imino]-ethane-2,1-diyl}-oxy)-ethane-2,1-diyl]}-dicarbamate, dinitrate 1102 mg (1 mmol) of the title compound of Example 1c), 1083 mg (3 mmol) of lutetium nitrate and 10 ml of triethylamine are refluxed in 1000 ml of methanol for 24 hours. It is evaporated to the dry state, and the residue is purified on silica gel (mobile solvent: chloroform/methanol=20:1 (5:1).

Yield: 614 mg (44% of theory) of an amorphous powder

Elementary analysis:

| Cld: | C 43.85 | H 4.81 | N 10.82 | F 8.00 | Lu 12.29 |
|---|---|---|---|---|---|
| Fnd: | C 43.71 | H 5.03 | N 10.71 | F 7.87 | Lu 12.13 | e) $Lu^{3+}$ Complex of N,N'-{[9,10-diethyl-5,14-bis(3-hydroxypropyl)-4,15-dimethyl-8,11-imino-3,6: 16,13 dinitrilo-1,18-benzodiazacyclo-eicosine-20,21-diyl]-bis[({[oxy-(1-oxo-propane-3,1-diyl)-imino]-ethane-2,1-diyl}-oxy)-ethane-2,1-diyl]-diamine}, ditrifluoroacetate, dinitrate 600 mg (0.43 mmol) of the title compound of Example 1d) is dissolved in 50 ml of trifluoroacetic acid and stirred for 12 hours at room temperature. It is evaporated to the dry state in a vacuum, and the residue is absorptively precipitated with 100 ml of diethyl ether. After filtration and drying (40° C.) in a vacuum, 600 mg (98% of theory) of an amorphous powder is obtained.

Elementary analysis:

| Cld: | C 49.88 | H 5.92 | N 11.03 | Lu 12.53 |
|---|---|---|---|---|
| Fnd: | C 49.71 | H 6.11 | N 10.90 | Lu 12.39 | f) $Lu^{3+}$ Complex of N,N'-{[9,10-diethyl-5,14-bis(3-hydroxypropyl)-4,15-dimethyl-8,11-imino-3,6: 16,13 dinitrilo-1,18-benzodiazacyclo-eicosine-20,21-diyl]-bis[({[oxy-(1-oxo-propane-3,1-diyl)-imino]-ethane-2,1-diyl}-oxy)-ethane-2,1-diyl]}-diamide of [(3,6,9-tricarboxylato-3,6,9-triazaundecane-1,11-dioic acid-11-oyl), gadolinium complex, sodium salt], dichloride 807 mg (2 mmol) of DTPA-monoanhydride-ethyl ester and 86 mg (0.7 mmol) of 4-(dimethylamino)-pyridine are added to 0.5 g (0.35 mmol) of the title compound of Example 1e) and 30 g of pyridine in 50 ml of dimethylformamide. It is stirred for 24 hours at 50° C. It is evaporated to the dry state in a vacuum, the residue is taken up in 200 ml of water and brought to a pH of 13 with 2N sodium hydroxide solution. It is stirred for 6 hours at room temperature. It is set at pH 2 with 10% aqueous hydrochloric acid and evaporated to the dry state in a vacuum. The residue is chromatographed on RP-18. The ligand that is thus obtained is dissolved in 30 ml of water, and 109 mg (0.29 mmol) of gadolinium oxide is added. It is stirred at 60° C., and the pH is kept at 4 by adding 1N aqueous sodium hydroxide solution. The solution is filtered, and the filtrate is set at pH 7.2 with 1N aqueous sodium hydroxide solution. Then, it is freeze-dried.

Yield: 676 mg (86% of theory) of an amorphous solid

Water content: 7.9%

Elementary analysis:

| Cld: | C 40.64 | H 4.49 | N 9.35 | Cl 3.16 | Gd 14.00 | Na 2.05 | Lu 7.79 |
|---|---|---|---|---|---|---|---|
| Fnd: | C 40.49 | H 4.62 | N 9.18 | Cl 3.05 | Gd 13.84 | Na 1.77 | Lu 7.61 |

EXAMPLE 2

$Lu^{3+}$ Complex of N,N'-{[(9,10-diethyl-5,14-bis(3-hydroxypropyl)-4,15-dimethyl-8,11-imino-3,6: 16,13 dinitrilo-1,18-benzodiazacyclo-eicosine-20,21-diyl]-bis[({[oxy-(1-oxo-propane-3,1-diyl)-imino]-ethane-2,1-diyl}-oxy)-ethane-2,1-diyl]}-diamide of [1,4,7-tetraazacyclododecane-1,4,7-tris(carboxylatomethyl)-10-(4-aza-3-oxo-nonan-2-yl-6-oyl)-gadolinium complex], dichloride 1.26 g (2 mmol) of the Gd complex of 10-(4-carboxy-2-oxo-3-azabutyl)-1,4,7,10-tetraazacyclododecane-1,4,7-triacetic acid, 0.17 g of lithium chloride (4 mmol) and 0.35 g (3 mmol) of N-hydroxysuccinimide are dissolved in 20 ml of dimethyl sulfoxide at 50° C. After cooling to room temperature, 0.62 g (3 mmol) of N,N'-dicyclohexylcarbodiimide is added and preactivated for 60 minutes. 712 mg (0.5 mmol) of the title compound that is described in Example 1e) and 0.2 g (2 mmol) of triethylamine are added to the N-hydroxysuccinimide ester solution that is thus produced and stirred overnight at room temperature. The suspension that is obtained is then mixed with sufficient acetone until precipitation occurs, the precipitate is suctioned off, dried, taken up in water, insoluble dicyclohexylurea is filtered out, and the filtrate is chromatographed on RP-18 (mobile solvent: gradient consisting of tetrahydrofuran/water).

Yield: 817 mg (81% of theory) of an amorphous powder

Water content: 7.8%

Elementary analysis (relative to anhydrous substance):

| Cld: | C 42.70 | H 4.70 | N 10.41 | Gd 15.58 | Cl 3.51 | Lu 8.67 |
|---|---|---|---|---|---|---|
| Fnd: | C 42.72 | H 4.85 | N 10.27 | Gd 15.41 | Cl 3.40 | Lu 8.52 |

EXAMPLE 3 a) $Zn^{2+}$ Complex of di-t-butyl-N,N'-{[9,10-diethyl-5,14-bis(3-hydroxypropyl)-4,15-dimethyl-8,11-imino-3:6:16,13-dinitrilo-1,18-benzodiazacyclo-eicoscin-20,21-diyl]-bis[({[oxy-(1-oxo -propane-3,1-diyl)-imino]-ethane-2,1-diyl}-oxy)-ethane-2,1-diyl]}-dicarbamate, nitrate 1102 mg (1 mmol) of the title compound of Example 1c), 568.2 mg (3 mmol) of zinc nitrate and 10 ml of triethylamine are refluxed in 1000 ml of methanol for 24 hours. It is evaporated to the dry state, and the residue is purified on silica gel (mobile solvent: chloroform/methanol→20:1 (5:1).

Yield: 0.563 g (46% of theory) of an amorphous powder

Elementary analysis:

| Cld: | C 56.88 | H 6.75 | N 11.44 | Zn 5.34 |
|---|---|---|---|---|
| Fnd: | C 56.69 | H 6.81 | N 11.24 | Zn 5.18 | b) $Zn^{2+}$ Complex of N,N'-{[9,10-diethyl-5,14-bis(3-hydroxypropyl)-4,15-dimethyl-8,11-imino-3:6:16,13-dinitrilo-1,18-benzodiazacyclo-eicoscin-20,21-diyl]-bis[({[oxy-(1-oxo-propane-3,1-diyl)-imino]-ethane-2,1-diyl}-oxy)-ethane-2,1-diyl]-diamine}, ditrifluoroacetate, nitrate 550 mg (0.45 mmol) of the title compound of Example 3a) is dissolved in 50 ml of trifluoroacetic acid and stirred for 8 hours at room temperature. It is evaporated to the dry state in a vacuum, and the residue is absorptively precipitated with 100 ml of diethyl ether. After filtration and drying (40° C.) in a vacuum, 0.557 g (99% of theory) of a crystalline powder is obtained.

Elementary analysis:

| Cld: | C 49.86 | H 5.47 | N 11.18 | F 9.10 | Zn 5.22 |
|---|---|---|---|---|---|
| Fnd: | C 49.71 | H 5.62 | N 11.03 | F 8.95 | Zn 5.12 |

$Zn^{2+}$ Complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl-bis[({[oxy-(1-oxo-propane-3,1-diyl)-imino]-ethane-2,1-diyl}-oxy)-ethane-2,1-diyl]}-diamide of [(3,6,9-tricarboxylato-3, 6,9-triazaundecane-1,11 dioic acid-11-oyl, gadolinium complex, sodium salt], chloride 807 mg (2 mmol) of DTPA-monoanhydride ethyl ester and 86 mg (0.7 mmol) of 4-(dimethylamino)-pyridine are added to 438.4 mg (0.35 mmol) of the title compound of Example 3b) and 30 g of pyridine in 50 ml of dimethylformamide. It is stirred for 24 hours at 50° C. It is evaporated to the dry state in a vacuum, the residue is taken up in 200 ml of water and brought to pH 13 with 2N sodium hydroxide solution. It is stirred for 6 hours at room temperature. It is set at pH 2 with 10% aqueous hydrochloric acid and evaporated to the dry state in a vacuum. The residue is chromatographed on RP-18 (mobile solvent: gradient consisting of tetrahydrofuran/water). The ligand that is thus obtained is dissolved in 30 ml of water, and 112 mg (0.31 mmol) of gadolinium oxide is added. It is stirred at 60° C., and the pH is kept at 4 by adding 1N aqueous sodium hydroxide solution. The solution is filtered, and the filtrate is set at pH 7.2 with 1N aqueous sodium hydroxide solution. Then, it is freeze-dried.

Yield: 0.654 g (89% of theory) of an amorphous solid
Elementary analysis (relative to anhydrous substance):

| Cld: | C 43.45 | H 4.80 | N 10.00 | Cl 1.69 | Gd 14.97 | Na 2.19 | Zn 3.11 |
|---|---|---|---|---|---|---|---|
| Fnd: | C 43.28 | H 4.95 | N 9.87 | Cl 1.53 | Gd 14.80 | Na 1.88 | Zn 3.02 |

EXAMPLE 4

$Zn^{2+}$ Complex of N,N'-{(9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis[({[oxy-(1-oxo-propane-3,1-diyl)-imino]-ethane-2,1-diyl}-oxy)-ethane-2,1-diyl]}-diamide of [1,4,7,10-tetraazacyclododecane-1,4,7-tris(carboxylatomethyl)-10-(4-aza-3-oxo-nona-2-yl-6-oyl), gadolinium complex], chloride 1.26 g (2 mmol) of the Gd complex of 10-(4-carboxy-2-oxo-3-azabutyl)-1,4,7,10-tetraazacyclododecane-1,4,7-triacetic acid, 0.17 g of lithium chloride (4 mmol) and 0.35 g (3 mmol) of N-hydroxysuccinimide are dissolved in 20 ml of dimethyl sulfoxide at 50° C. After cooling to room temperature, 0.62 g (3 mmol) of N,N'-dicyclohexylcarbodiimide is added and preactivated for 60 minutes. 626 mg (0.5 mmol) of the title compound that is described in Example 3b) and 0.2 g (2 mmol) of triethylamine are added to the N-hydroxysuccinimide ester solution that is thus produced, and it is stirred overnight at room temperature. The suspension that is obtained is then mixed with sufficient acetone until precipitation occurs, the precipitate is suctioned off, dried, taken up in water, insoluble dicyclohexylurea is filtered out, and the filtrate is chromatographed on RP-18 (mobile solvent: gradient consisting of tetrahydrofuran/water).

Yield: 0.74 g (79% of theory) of an amorphous powder
Water content: 9.2%
Elementary analysis (relative to anhydrous substance):

| Cld: | C 46.17 | H 5.06 | N 11.22 | Gd 16.79 | Cl 1.89 | Zn 3.49 |
|---|---|---|---|---|---|---|
| Fnd: | C 46.02 | H 5.21 | N 11.11 | Gd 16.65 | Cl 1.72 | Zn 3.37 |

EXAMPLE 5 a) Di-t-butyl-N,N'-([(4,5-dinitrobenzene-1,2-diyl)-dioxy]-bis{[(1-oxo-propane-3,1-diyl)-imino]-ethane-2,1-diyl})-dicarbamate 13.34 g (3.5 mmol) of 3,3'(4,5-dinitro-benzene-1,2-diyldioxy)-dipropanoyl chloride, produced from dicarboxylic acid with thionyl chloride/pyridine, as described in U.S. Pat. No. 5,504,205, is dissolved in 50 ml of dry dichloromethane and reacted with the mixture consisting of 561 mg (3.5 mmol) of N-t-butoxycarbonyl-1,2-diaminoethane, produced according to J. Org. Chem., 46, 2455 (1981), and 558 mg (7.05 mmol) of dry pyridine in 25 ml of dry dichloromethane while being stirred. It is allowed to stir for one more hour, washed with 1N hydrochloric acid, sodium bicarbonate solution, and the solution is dried on sodium sulfate. Then, it is evaporated to the dry state in a vacuum, and the residue is purified by chromatography on silica gel. As eluants, mixtures of hexane/ethyl acetate of increasing polarity are used. The product-containing fractions are combined and evaporated to the dry state in a vacuum. 1.890 g (85.9% of theory) of the title compound is obtained.

Elementary analysis:

| Cld: | C 49.68 | H 6.41 | N 13.37 |
|---|---|---|---|
| Fnd: | C 49.79 | H 6.50 | N 13.30 | b) Di-t-butyl-N,N'-([(4,5-diaminobenzene-1,2-diyl)-dioxy]-bis{[(1-oxo-propane-3,1-diyl)-imino]-ethane-2,1-diyl})-dicarbamate 1.896 g (3 mmol) of the dinitro compound that is produced under 5a) is added to 50 ml of dry dichloromethane. It is mixed with 100 mg of 10% Pd/C and refluxed. Then, 1.47 ml (30.1 mmol) of hydrazine hydrate is added in drops to 5 ml of dry ethanol while being stirred. The heating is continued until the dark solution becomes considerably lighter. The study of a thin-layer sample indicates that a polar product has formed and that starting material is no longer present. It is hot-filtered through a layer of diatomaceous earth, rewashed with hot, dry ethanol and evaporated to the dry state. The title compound is obtained as a light powder.

Yield: 1.60 g (93.7% of theory)
Elementary analysis:

| Cld: | C 54.92 | H 7.80 | N 14.78 |
| --- | --- | --- | --- |
| Fnd: | C 54.83 | H 7.88 | N 14.91 | c) Di-t-butyl-N,N-{[9,10-diethyl-5,14-bis(3-hydroxypropyl)-4,15-dimethyl-3,6:8:11:3,6: 13,16-triimino-1,18-benzodiazacyclo-eicosane-20,21-diyl]-bis{[oxy-(1-oxo-propane-3,1-diyl)-imino]-ethane-2,1-diyl}}-dicarbamate 722.4 mg (1.5 mmol) of the 2,5-bis[(5-formyl-3-hydroxypyrrole-4-methylpyrrol-2-yl)-methyl]-3,4-diethyl pyrrole and 853 mg (1.5 mmol) of the diamine that is produced under 5b are dissolved while being heated in a mixture consisting of 1.6 l of oxygen-pure dry benzene that is flushed with argon and 200 ml of dry methanol. Then, 50 ml of dry methanol, in which 0.5 ml of concentrated hydrochloric acid is dissolved, is added and refluxed under argon cover gas for 24 hours. It is allowed to cool, neutralized by the addition of 120 mg of powdered potassium carbonate and filtered by magnesium sulfate. It is evaporated to the dry state in a vacuum, the residue is taken up in dichloromethane and purified by chromatography on silica gel. The title compound is eluted with mixtures of hexane/ethyl acetate.

Yield: 1.315 g (86.4% of theory)
Elementary analysis:

| Cld: | C 63.95 | H 7.85 | N 12.43 |
| --- | --- | --- | --- |
| Fnd: | C 64.12 | H 7.96 | N 12.52 | d) $Lu^{3+}$ Complex of di-t-butyl-N,N'-{[9,10-diethyl-5,14-bis(3-hydroxypropyl)-4,5-dimethyl-8,11-imino-3,6: 16,13-dinitrilo-1,18-benzodiazacyclo-eicosine-20,21-diyl]-bis{[oxy-(1-oxo-propane-3,1-diyl)-imino]-ethane-2,1-diyl}}-dicarbamate, dinitrate 1014 mg (1 mmol) of the title compound of Example 5c), 568.2 mg (3 mmol) of lutetium nitrate and 10 ml of triethylamine are refluxed in 1000 ml of methanol for 24 hours. It is evaporated to the dry state, and the residue is purified on silica gel (mobile solvent: chloroform/methanol→20:1 (5:1).

Yield: 0.563 g (43% of theory) of an amorphous powder
Elementary analysis:

| Cld: | C 49.58 | H 5.70 | N 11.78 | Lu 13.37 |
| --- | --- | --- | --- | --- |
| Fnd: | C 49.39 | H 5.83 | N 11.64 | Lu 13.24 | e) $Lu^{3+}$ Complex of N,N'-{[9,10-diethyl-5,14-bis(3-hydroxypropyl)-4,15-dimethyl-8,11-imino-3,6: 16,13 dinitrilo-1,18-benzodiazacyclo-eicosine-20,21-diyl)]-bis{[oxy-(1-oxo-propane-3,1-diyl)-imino]-ethane-2,1-diyl}-diamine, ditrifluoroacetate, dinitrate 0.55 g (0.42 mmol) of the title compound of Example 5d) is dissolved in 50 ml of trifluoroacetic acid and stirred for 8 hours at room temperature. It is evaporated to the dry state in a vacuum, and the residue is absorptively precipitated with 100 ml of diethyl ether. After filtration and drying (40° C.) in a vacuum, 600 mg (98% of theory) of an amorphous powder is obtained.

Elementary analysis:

| Cld: | C 43.15 | H 4.53 | N 11.53 | F 8.53 | Lu 13.10 |
| --- | --- | --- | --- | --- | --- |
| Fnd: | C 43.01 | H 4.71 | N 11.38 | F 8.37 | Lu 12.93 | f) $Lu^{3+}$ Complex of N,N'-{[9,10-diethyl-5,14-bis(3-hydroxypropyl)-4,15-dimethyl-8,11-imino-3,6: 16,13 dinitrilo-1,18-benzodiazacyclo-eicosine-20,21-diyl]-bis{[oxy-(1-oxo-propane-3,1-diyl)-imino]-ethane-2,1-diyl}-diamide of [(3,6,9-tricarboxylato-3,6,9-triazaundecane-1,11-dioic acid-11-oyl), gadolinium complex, disodium salt], dichloride 807 mg (2 mmol) of DTPA-monoanhydride ethyl ester and 86 mg (0.7 mmol) of 4-(dimethylamino)-pyridine are added to 467.6 mg (0.35 mmol) of the title compound of Example 5e) and 30 g of pyridine in 50 ml of dimethylformamide. It is stirred for 24 hours at 50° C. It is evaporated to the dry state in a vacuum, the residue is taken up in 200 ml of water and brought to pH 13 with 2N sodium hydroxide solution. It is stirred for 6 hours at room temperature. It is set at pH 2 with 10% aqueous hydrochloric acid and evaporated to the dry state in a vacuum. The residue is chromatographed on RP-18. The ligand that is thus obtained is dissolved in 30 ml of water, and 109 mg (0.30 mmol) of gadolinium oxide is added. It is stirred at 60° C., and the pH is kept at 4 by adding 1N aqueous sodium hydroxide solution. The solution is filtered, and the filtrate is set at pH 7.2 with 1N aqueous sodium hydroxide solution. Then, it is freeze-dried.

Yield: 0.65 g (86% of theory) of an amorphous solid
Water content: 10.3%
Elementary analysis (relative to anhydrous substance):

| Cld: | C 40.07 | H 4.30 | N 9.74 | Cl 3.29 | Gd 14.75 | Na 2.13 | Lu 8.11 |
| --- | --- | --- | --- | --- | --- | --- | --- |
| Fnd: | C 39.88 | H 4.49 | N 9.61 | Cl 3.12 | Gd 14.38 | Na 1.88 | Lu 8.02 |

EXAMPLE 6

$Lu^{3+}$ Complex of N,N'-{[9,10-diethyl-5,14-bis(3-hydroxypropyl)-4,15-dimethyl-8,11-imino-3,6: 16,13 dinitrilo-1,18-benzodiazacyclo-eicosine-20,21-diyl]-bis{[oxy-(1-oxo-propane-3,1-diyl)-imino]-ethane-2,1-diyl}-diamide of {1,4,7,10-tetraazacyclododecane-1,4,7-tris(carboxylatomethyl)-10-(4-aza-3-oxo-nonan-2-yl-6-oyl), gadolinium complex], dichloride 1.26 g (2 mmol) of the Gd complex of 10-(4-carboxy-2-oxo-3-azabutyl)-1,4,7,10-tetraazacyclododecane-1,4,7-triacetic acid, 0.17 g of lithium chloride (4 mmol) and 0.35 g (3 mmol) of N-hydroxysuccinimide are dissolved in 20 ml of dimethyl sulfoxide at 50° C. after cooling to room temperature, 0.62 g (3 mmol) of N,N'-dicyclohexylcarbodiimide is added and preactivated for 60 minutes. 668 mg (0.5 mmol) of the title compound that is described in Example 5e) and 0.2 g (2 mmol) of triethylamine are added to the N-hydroxysuccinimide ester solution that is thus produced, and it is stirred overnight at room temperature. The suspension that is obtained is then mixed with sufficient acetone until precipitation occurs, the precipitate is suctioned off, dried, taken up in water, insoluble dicyclohexylurea is filtered off, and the filtrate is chromatographed on RP-18 (mobile solvent: gradient consisting of tetrahydrofuran/water).

Yield: 0.81 g (84% of theory) of an amorphous powder
Water content: 9.4%
Elementary analysis (relative to anhydrous substance):

| Cld: | C 42.32 | H 4.49 | N 10.89 | Gd 16.30 | Cl 3.67 | Lu 9.07 |
|---|---|---|---|---|---|---|
| Fnd: | C 42.17 | H 4.62 | N 10.67 | Gd 16.13 | Cl 3.48 | Lu 8.91 |

EXAMPLE 7 a) $Zn^{2+}$ Complex of di-t-butyl-N,N'-{[9,10-diethyl-5,14-bis(3-hydroxypropyl)-4,5-dimethyl-8,11-imino-3:6:16,13-dinitrilo-1,18-benzodiazacyclo-eicoscin-20,21-diyl)-bis{[oxy-(1-oxo-propane-3,1-diyl)-imino]-ethane-2,1-diyl}}-dicarbamate, nitrate 1014 mg (1 mmol) of the title compound of Example 5c), 568.3 mg (3 mmol) of zinc nitrate and 10 ml of triethylamine are refluxed in 1000 ml of methanol for 24 hours. It is evaporated to the dry state, and the residue is purified on silica gel (mobile solvent: chloroform/methanol→20:1 (5:1).

Yield: 534 mg (47% of theory) of an amorphous powder
Elementary analysis:

| Cld: | C 57.06 | H 6.56 | N 12.32 | Zn 5.75 |
|---|---|---|---|---|
| Fnd: | C 56.92 | H 6.73 | N 12.17 | Zn 5.68 | b) $Zn^{2+}$ Complex of N,N'-{[9,10-diethyl-5,14-bis(3-hydroxypropyl)-4,15-dimethyl-8,11-imino-3:6:16,13-dinitrilo-1,18-benzodiazacyclo-eicoscin-20,21-diyl)-bis{[oxy-(1-oxo-propane-3,1-diyl)-imino]-ethane-2,1-diyl]}-diamine, ditrifluoroacetate, nitrate 0.52 mg (0.458 mmol) of the title compound of Example 7a) is dissolved in 50 ml of trifluoroacetic acid and stirred for 8 hours at room temperature. It is evaporated to the dry state in a vacuum, and the residue is stirred with 100 ml of diethyl ether. After filtration and drying (40° C.) in a vacuum, 527 mg (99% of theory) of an amorphous powder is obtained.
Elementary analysis:

| Cld: | C 49.51 | H 5.19 | N 12.03 | F 9.79 | Zn 5.61 |
|---|---|---|---|---|---|
| Fnd: | C 49.38 | H 5.35 | N 11.91 | F 9.63 | Zn 5.49 | c) $Zn^{2+}$ Complex of N,N'-{[9,10-diethyl-5,14-bis(3-hydroxypropyl)-4,15-dimethyl-8,11-imino-3,6: 16,13-dinitrilo-1,18-benzodiazacyclo-eicosine-20,21-diyl]-bis{[oxy-(1-oxo-propane-3,1-diyl)-imino]-ethane-2,1-diyl}-diamide of the [(3,6,9-tricarboxylato-3,6,9-triazaundecane-1,11 dioic acid-11-oyl), gadolinium complex, sodium salt], chloride 807 mg (2 mmol) of DTPA-monoanhydride ethyl ester and 86 mg (0.7 mmol) of 4-(dimethylamino)-pyridine are added to 407.5 mg (0.35 mmol) of the title compound of Example 7b) and 30 g of pyridine in 50 ml of dimethylformamide. It is stirred for 24 hours at 50° C. It is evaporated to the dry state in a vacuum, the residue is taken up in 200 ml of water and brought to pH 13 with 2N sodium hydroxide solution. It is stirred for 6 hours at room temperature. It is set at pH 2 with 10% aqueous hydrochloric acid and evaporated to the dry state in a vacuum. The residue is chromatographed on RP-18. The ligand that is thus obtained is dissolved in 30 ml of water, and 109 mg (0.30 mmol) of gadolinium oxide is added. It is stirred at 60° C., and the pH is kept at 4 by adding 1N aqueous sodium hydroxide solution. The solution is filtered, and the filtrate is set at pH 7.2 with 1N aqueous sodium hydroxide solution. Then, it is freeze-dried.

Yield: 0.61 mg (86% of theory) of an amorphous solid
Water content: 7.8%
Elementary analysis (relative to anhydrous substance):

| Cld: | C 42.96 | H 4.61 | N 10.44 | Cl 1.76 | Gd 15.62 | Na 2.28 | Zn 3.25 |
|---|---|---|---|---|---|---|---|
| Fnd: | C 42.81 | H 4.75 | N 10.28 | Cl 1.68 | Gd 15.54 | Na 2.01 | Zn 3.16 |

EXAMPLE 8

$Zn^{2+}$ Complex of N,N'-{[9,10-diethyl-5,14-bis(3-hydroxypropyl)-4,15-dimethyl-8,11-imino-3,6: 16,13-dinitrilo-1,18-benzodiazacyclo-eicosine-20,21-diyl]-bis{[oxy-(1-oxo-propane-3,1-diyl)-imino]-ethane-2,1-diyl}-diamide of [1,4,7,10-tetraazacyclododecane-1,4,7-tris(carboxylatomethyl)-10-(4-aza-3-oxo-nonan-2-yl-6-oyl), gadolinium complex], chloride 1.26 g (2 mmol) of the Gd complex of 10-(4-carboxy-2-oxo-3-azabutyl)-1,4,7,10-tetraazacyclododecane-1,4,7-triacetic acid, 0.17 g of lithium chloride (4 mmol) and 0.35 g (3 mmol) of N-hydroxysuccinimide are dissolved in 20 ml of dimethyl sulfoxide at 50° C. After cooling to room temperature, 0.62 g (3 mmol) of N,N'-dicyclohexylcarbodiimide is added and preactivated for 60 minutes. 712 mg (0.5 mmol) of the title compound that is described in Example 7b) and 0.2 g (2 mmol) of triethylamine are added to the N-hydroxysuccinimide ester solution that is thus produced, and it is stirred overnight at room temperature. The suspension that is obtained is then mixed with sufficient acetone until precipitation occurs, the precipitate is suctioned off, dried, taken up in water, insoluble dicyclohexylurea is filtered off, and the filtrate is chromatographed on RP-18 (mobile solvent: gradient consisting of tetrahydrofuran/water).

Yield: 0.73 g (82% of theory) of an amorphous powder
Water content: 10.1%
Elementary analysis (relative to anhydrous substance):

| Cld: | C 45.76 | H 4.86 | N 11.77 | Gd 17.62 | Cl 1.99 | Zn 3.66 |
|---|---|---|---|---|---|---|
| Fnd: | C 45.61 | H 5.07 | N 11.61 | Gd 17.48 | Cl 1.81 | Zn 3.48 |

EXAMPLE 9 a) t-Butyl-N-(2-{2-[2-(tosyloxy)-ethoxy]-ethoxy}-ethyl)-carbamate 4.666 g (20 mmol) of N-{2-[2-(2-hydroxyethoxy)-ethoxy]-ethyl}-carbamic acid-t-butyl ester, produced according to Helv. Chim. Acta, 74, 1697 (1991), as well as 1.582 g (20 mmol) of dry pyridine are dissolved in 60 ml of dry dichloromethane. While being cooled and in a moisture-free environment, 3.813 g (20 mmol) of p-toluenesulfonyl chloride in 20 ml of dichloromethane is added in drops. It is allowed to stir overnight, washed with 1N hydrochloric acid with sodium bicarbonate solution, and the solution is dried on sodium sulfate. Then, dessicant is suctioned off, it is evaporated to the dry state in a vacuum, and the residue is purified by chromatography on silica gel. Mixtures of hexane in increasing addition of ethyl acetate are used as eluants. The product-containing fractions are combined and concentrated by evaporation in a vacuum. 6.40 g (82.6% of theory) of the title compound is obtained.
Elementary analysis:

| Cld: | C 55.78 | H 7.54 | N 3.61 |
|---|---|---|---|
| Fnd: | C 55.70 | H 7.62 | N 3.69 | b) Di-t-butyl-N,N'-{[(4,5-dinitrobenzene-1,2-diyl)-dioxy]-[({[(ethane-2,1-diyl)-oxy]-ethane-2,1-diyl}-oxy)-ethane-2,1-diyl]}-dicarbamate 1.601 g (8 mmol) of 1,2-dihydroxy-4,5-dinitrobenzene, produced according to U.S. Pat. No. 5,504,205, is dissolved in 50 ml of dry benzene with argon cover gas and mixed with 898 mg (16 mmol) of powdered potassium hydroxide. It is refluxed, and the solution of 6.200 g (16 mmol) of the tosylate that is produced under 9a) in 20 ml of dry benzene is then added in drops. The reaction is complete after 6 hours. After cooling, it is suctioned off through diatomaceous earth, rewashed with warm benzene, the solution is concentrated by evaporation in a vacuum, and the residue is subjected to column chromatography on silica gel. The title compound is eluted with mixtures of dichloromethane and ethanol. 3.043 g (57.4% of theory) of the title compound is obtained.
Elementary analysis:

| Cld: | C 50.75 | H 7.00 | N 8.45 |
|---|---|---|---|
| Fnd: | C 50.83 | H 7.11 | N 8.52 | c) Di-t-butyl-N,N'-{[(4,5-diaminobenzene-1,2-diyl)-dioxy]-[({[(ethane-2,1-diyl)-oxy]-ethane-2,1-diyl}-oxy)-ethane-2,1-diyl]}-dicarbamate 1.988 g (3 mmol) of the dinitro compound that is produced under Example 9b) is added to 50 ml of dry ethanol, mixed with 100 mg of 10% Pd/C and refluxed. Then, 1.47 ml (30.1 mmol) of hydrazine hydrate is added in drops to 5 ml of dry ethanol while being stirred. Heating is continued until the dark solution becomes considerably lighter. A thin-layer sample indicates that the starting material has disappeared and that a more polar product has formed. It is hot-filtered through a layer of diatomaceous earth, rewashed with hot, dry ethanol and evaporated to the dry state in a vacuum. The title compound is obtained as a light powder.
Yield: 1.696 g (93.8% of theory)
Elemenatary analysis:

| Cld: | C 55.80 | H 8.36 | N 9.30 |
|---|---|---|---|
| Fnd: | C 55.70 | H 8.45 | N 9.41 | d) Di-t-butyl-N,N'-{[9,10-diethyl-5,14-bis(3-hydroxypropyl)-4,15-dimethyl-3,6: 8,11: 13,16 triimino-1,18-benzodiazacyclo-eicosane-20,21-diyl]-bis[({[oxy-(ethane-2,1-diyl)-oxy]-ethane-2,1-diyl}-oxy)-ethane-2,1-diyl]}-dicarbamate 722.4 mg (1.5 mmol) of the 2,5-bis[(5-formyl-3-hydroxypyrrole-4-methylpyrrol]-2-yl)-methyl]-3,4-diethylpyrrole that is produced according to U.S. Pat. No. 5,504,205 and 904.1 mg (1.5 mmol) of the diamine that is produced under Example 9c) are dissolved while being heated in a mixture of 1.6 l of oxygen-pure dry benzene that is flushed with argon and 200 ml of dry methanol. Then, 50 ml of dry methanol, in which 0.5 ml of concentrated hydrochloric acid is dissolved, is added, and it is refluxed for 24 hours under argon cover gas. It is allowed to cool, neutralized by adding 120 mg of powdered potassium carbonate and filtered by magnesium sulfate. It is evaporated to the dry state in a vacuum, the residue is taken up in dichloromethane and purified by chromatography on silica gel. The title compound is eluted with mixtures of hexane/ethyl acetate.
Yield: 1.332 g (84.7% of theory)
Elementary analysis:

| Cld: | C 64.16 | H 8.17 | N 9.35 |
|---|---|---|---|
| Fnd: | C 64.28 | H 8.28 | N 9.45 | e) $Lu^{3+}$ Complex of di-t-butyl-N,N'-{[9,10-diethyl-5,14-bis(3hydroxypropyl]-4,15-dimethyl-8,11-imino-3,6: 16,13-dinitrilo-1,18-benzodiazacyclo-eicosine-20,21-diyl]-bis[({[oxy-(ethane-2,1-diyl)-oxy]-ethane-2,1-diyl}-oxy)-ethane-2,1-diyl]}-dicarbamate, dinitrate 1048 mg (1 mmol) of the title compound of Example 9d), 1083 mg (3 mmol) of lutetium nitrate and 10 ml of triethylamine are refluxed in 1000 ml of methanol for 24 hours. It is evaporated to the dry state, and the residue is purified on silica gel (mobile solvent: chloroform/methanol→20:1 (5:1).
Yield: 0.56 g (42% of theory) of an amorphous powder
Elementary analysis:

| Cld: | C 50.11 | H 6.01 | N 9.39 | Lu 13.04 |
|---|---|---|---|---|
| Fnd: | C 49.93 | H 6.17 | N 9.26 | Lu 12.87 | f) $Lu^{3+}$ Complex of N,N'-[9,10-diethyl-5,14-bis(3-hydroxypropyl)-4,15-dimethyl-8,11-imino-3,6: 16,13-dinitrilo-1,18-benzodiazacyclo-eicoine-20,21-diyl]-bis[({[oxy-(ethane-2,1-diyl)-oxy]-ethane-2,1-diyl}-oxy)-ethane-2,1-diyl]}-diamine, ditrifluoroacetate, dinitrate 0.55 g (0.41 mmol) of the title compound of Example 9e) is dissolved in 50 ml of trifluoroacetic acid and stirred for 8 hours at room temperature. It is evaporated to the dry state in a vacuum, and the residue is absorptively precipitated with 100 ml of diethyl ether. After filtration and drying (40° C.) in a vacuum, 0.556 g (99% of theory) of an amorphous powder is obtained.
Elementary analysis:

| Cld: | C 43.83 | H 4.86 | N 9.20 | F 8.32 | Lu 12.77 |
|---|---|---|---|---|---|
| Fnd: | C 43.71 | H 4.99 | N 9.03 | F 8.18 | Lu 12.65 | g) $Lu^{3+}$ Complex of {[9,10-diethyl-5,14-bis(3-hydroxypropyl)-4,5-dimethyl-8,11-imino-3,6: 16,13-dinitrilo-1,18-benzodiazacyclo-eicosine-20,21-diyl]-bis[({[oxy-(ethane-2,1-diyl)-oxy]-ethane-2,1-diyl}-oxy)-ethane-2,1-diyl]}-diamide of [(3,6,9-tricarboxylato-3,6,9-triazaundecane-1,11-dioic acid-11-oyl), gadolinium complex, disodium salt], dichloride 807 mg (2 mmol) of DTPA-monoanhydride ethyl ester and 86 mg (0.7 mmol) of 4-(dimethylamino)-pyridine are added to 479.5 g (0.35 mmol) of the title compound of Example 9f) and 30 g of pyridine in 50 ml of dimethylformamide. It is stirred for 24 hours at 50° C. It is evaporated to the dry state in a vacuum, the residue is taken up in 200 ml of water and brought to pH 13 with 2N sodium hydroxide solution. It is stirred for 6 hours at room temperature. It is set at pH 2 with 10% aqueous hydrochloric acid and evaporated to the dry state in a vacuum. The residue is chromatographed on RP-18. The ligand that is thus obtained is dissolved in 30 ml of water, and 109 mg (0.29 mmol) of gadolinium oxide is added. It is stirred at 60° C., and the pH is kept at 4 by adding 1N aqueous sodium hydroxide solution. The solution is filtered, and the filtrate is set at pH 7.2 with 1N aqueous sodium hydroxide solution. Then, it is freeze-dried.

Yield: 0.637 mg (83% of theory) of an amorphous solid
Water content: 9.6%
Elementary analysis (relative to anhydrous substance):

| Cld: | C 40.55 | H 4.51 | N 8.31 | Cl 3.23 | Gd 14.35 | Na 2.10 | Lu 7.98 |
|---|---|---|---|---|---|---|---|
| Fnd: | C 40.47 | H 4.70 | N 8.15 | Cl 3.10 | Gd 14.21 | Na 1.95 | Lu 7.81 |

EXAMPLE 10

$Lu^{3+}$ Complex of N,N'-{[9,10-diethyl-5,14-bis(3-hydroxypropyl)-4,15-dimethyl-8,11-imino-3,6: 16,13-dinitrilo-1,18-benzodiazacyclo-eicosine-20,21-diyl]-bis[({[oxy-(ethane-2,1- diyl)-oxy]-ethane-2,1-diyl}-oxy)-ethane-2,1-diyl]}-diamide of [1,4,7,10-tetraazacyclododecane-1,4,7-tris(carboxylatomethyl)-10-(4-aza-3-oxo-nonan-2-yl-6-oyl), gadolinium complex], dichloride 1.26 g (2 mmol) of the Gd complex of 10-(4-carboxy-2-oxo-3-azabutyl)-1,4,7,10-tetraazacyclododecane-1,4,7-triacetic acid, 0.17 g (4 mmol) of lithium chloride and 0.35 g (3 mmol) of N-hydroxy succinimide are dissolved in 20 ml of dimethyl sulfoxide at 50° C. After cooling to room temperature, 0.62 g (3 mmol) of N,N'-dicyclohexylcarbodimide is added and preactivated for 60 minutes. 685 mg (0.5 mmol) of the title compound that is described in Example 9f) and 0.2 g (2 mmol) of triethylamine are added to the N-hydroxysuccinimide ester solution that is thus produced, and it is stirred overnight at room temperature. The suspension that is obtained is then mixed with sufficient acetone until precipitation occurs, the precipitate is suctioned off, dried, taken up in water, insoluble dicyclohexylurea is filtered out, and the filtrate is chromatographed on RP-18 (mobile solvent: gradient consisting of tetrahydrofuran/water).

Yield: 0.925 g (80% of theory) of an amorphous powder
Water content: 8.7%
Elementary analysis (relative to anhydrous substance):

| Cld: | C 43.63 | H 5.23 | N 10.30 | Gd 13.60 | Cl 3.07 | Lu 7.57 |
|---|---|---|---|---|---|---|
| Fnd: | C 43.54 | H 5.41 | N 10.17 | Gd 13.47 | Cl 2.89 | Lu 7.41 |

EXAMPLE 11 a) $Zn^{2+}$ Complex of di-t-butyl-N,N'-{[9,10-diethyl-5,14-bis(3-hydroxypropyl)-4,15-dimethyl-8,11-imino-3:6:16,13-dinitrilo-1,18-benzodiazacyclo-eicoscin-20,21-diyl]-bis[({[oxy-(ethane-2,1-diyl)-oxy]-ethane-2,1-diyl}-oxy)-ethane-2,1-diyl]}-carbamate, nitrate 1048 mg (1 mmol) of the title compound of Example 9d), 568.3 mg (3 mmol) of zinc nitrate and 10 ml of triethylamine are refluxed in 1000 ml of methanol for 24 hours. It is evaporated to the dry state, and the residue is purified on silica gel (mobile solvent: chloroform/methanol→20:1 (5:1).

Yield: 0.492 g (42% of theory) of an amorphous powder
Elementary analysis:

| Cld: | C 57.46 | H 6.89 | N 9.57 | Zn 5.58 |
|---|---|---|---|---|
| Fnd: | C 57.28 | H 7.03 | N 9.48 | Zn 5.47 | b) $Zn^{2+}$ Complex of N,N'-{[9,10-diethyl-5,14-bis(3-hydroxypropyl)-4,15-dimethyl-8,11-imino-3:6:16,13-dinitrilo-1,18-benzodiazacyclo-eicoscin-20,21-diyl]-bis[({[oxy-(ethane-2,1-diyl)-oxy]-ethane-2,1-diyl}-oxy)-ethane-2,1-diyl]-diamine}, ditrifluoroacetate, nitrate 0.49 g (0.419 mmol) of the title compound of Example 11a) is dissolved in 50 ml of trifluoroacetic acid and stirred for 8 hours at room temperature. It is evaporated to the dry state in a vacuum, and the residue is absorptively precipitated with 100 ml of diethyl ether. After filtration and drying (40° C.) in a vacuum, 0.497 mg (99% of theory) of an amorphous powder is obtained.

Elementary analysis:

| Cld: | C 50.11 | H 5.55 | N 9.35 | F 9.51 | Zn 5.46 |
|---|---|---|---|---|---|
| Fnd: | C 50.01 | H 5.71 | N 9.18 | F 9.41 | Zn 5.36 | c) $Zn^{2+}$ Complex of N,N'-{[9,10-diethyl-5,14-bis(3-hydroxypropyl)-4,15-dimethyl-8,11-imino-3,6: 16,13-dinitrilo-1,18-benzodiazacyclo-eicosine-20,21-diyl]-bis[({[oxy-(ethane-2,1-diyl)-oxy]-ethane-2,1-diyl}-oxy)-ethane-2,1-diyl]}-diamide of [(3,6,9-tricarboxylato-3,6,9-triazaundecane-1,11 dioic acid-11-oyl), gadolinium complex, sodium salt], chloride 807 mg (2 mmol) of DTPA-monoanhydride ethyl ester and 86 mg (0.7 mmol) of 4-(dimethylamino)-pyridine are added to 419.5 mg (0.35 mmol) of the title compound of Example 11b) and 30 g of pyridine in 50 ml of dimethylformamide. It is stirred for 24 hours at 50° C. It is evaporated to the dry state in a vacuum, the residue is taken up in 200 ml of water and brought to pH 13 with 2N sodium hydroxide solution. It is stirred for 6 hours at room temperature. It is set at pH 2 with 10% aqueous hydrochloric acid and evaporated to the dry state in a vacuum. The residue is chromatographed on RP-18. The ligand that is thus obtained is dissolved in 30 ml of water, and 109 mg (0.29 mmol) of gadolinium oxide is added. It is stirred at 60° C., and the pH is kept at 4 by adding 1N aqueous sodium hydroxide solution. The solution is filtered, and the filtrate is set at pH 7.2 with 1N aqueous sodium hydroxide solution. Then, it is freeze-dried.

Yield: 0.638 g (89% of theory) of an amorphous solid
Water content: 7.5%
Elementary analysis (relative to anhydrous substance):

| Cld: | C 43.42 | H 4.83 | N 8.90 | Cl 1.73 | Gd 15.36 | Na 2.25 | Zn 3.19 |
|---|---|---|---|---|---|---|---|
| Fnd: | C 43.27 | H 4.97 | N 8.72 | Cl 1.64 | Gd 15.21 | Na 2.03 | Zn 3.05 |

EXAMPLE 12

$Zn^{2+}$ Complex of N,N'-{[9,10-diethyl-5,14-bis(3-hydroxypropyl)4,15-dimethyl-8,11-imino-3,6: 16,13 (dinitrilo-1,18-benzodiazacyclo-eicosine-20,21-diyl]-bis[({[oxy-(ethane-2,1-diyl)-oxy]-ethane-2,1-diyl}-oxy)-ethane-2,1-diyl]}-diamide of [1,4,7,10-tetraazacyclododecane-1,4,7-tris(carboxylatomethyl)-10-(4-aza-3-oxo-nona-2-yl-6-oyl)-gadolinium complex], chloride 1.26 g (2 mmol) of the Gd complex of 10-(4-carboxy-2-oxo-3-azabutyl)-1,4,7,10-tetraazacyclododecane-1,4,7-triacetic acid, 0.17 g of lithium chloride (4 mmol) and 0.35 g (3 mmol) of N-hydroxysuccinimide are dissolved in 20 ml of dimethyl sulfoxide at 50° C. After cooling to room temperature, 0.62 g (3 mmol) of N,N'-dicyclohexylcarbodiimide is added and preactivated for 60 minutes. 599.2 mg (0.5 mmol) of the title compound that is described in Example 11b) and 0.2 g (2 mmol) of triethylamine are added to the N-hydroxysuccinimide ester solution, and it is stirred overnight at room temperature. The suspension that is obtained is then mixed with sufficient acetone until precipitation occurs, the precipitate is suctioned off, dried, taken up in water, insoluble dicyclohexylurea is filtered out, and the filtrate is chromatographed on RP-18 (mobile solvent: gradient consisting of tetrahydrofuran/water).

Yield: 0.867 mg (80% of theory) of an amorphous powder

Water content: 9.0%

Elementary analysis (relative to anhydrous substance):

| Cld: | C 46.55 | H 5.58 | N 10.99 | Gd 14.51 | Cl 1.64 | Zn 3.02 |
|---|---|---|---|---|---|---|
| Fnd | C 46.51 | H 5.69 | N 10.81 | Gd 14.38 | Cl 1.52 | Zn 2.88 |

What is claimed is:

1. A metalloporphyrin complex compound according to formula I

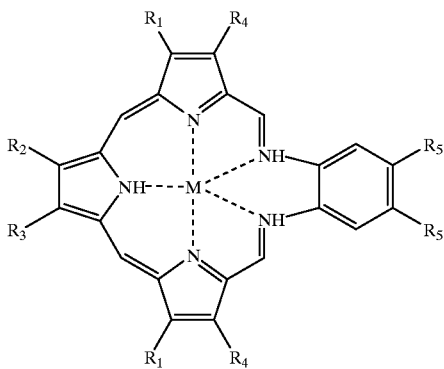

wherein

M is an ion of a diagmagnetic metal, $R^1$, $R^2$, $R^3$ and $R^4$ are each, independently of one another, a hydrogen atom, a $C_1$–$C_{30}$ alkyl, a $C_1$–$C_{30}$ alkyl which is interrupted by 1–10 oxygen atoms, a $C_1$–$C_{30}$ alkyl which is substituted with 1–5 hydroxy groups or 1–2 COOH groups, or a $C_1$–$C_{30}$ alkyl which is interrupted by 1–10 oxygen atoms and substituted by 1–5 hydroxy groups or 1–2-COOH groups, $R^5$ is —(O)$_{0,1}$—L—NH—K, L is a straight-chain or branched $C_1$–$C_{20}$ alkylene, which optionally is interrupted by 1–8 oxygen atoms, 1–5 NH groups, 1–5 CO groups, 1–5 NHCO groups, 1–5 CONH groups or 1–3 sulfur atoms, or L is 1–2 phenylene groups, K is a complexing agent of formulae (IIa), (IIb), (IIc) or (IId),

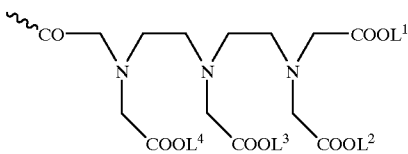

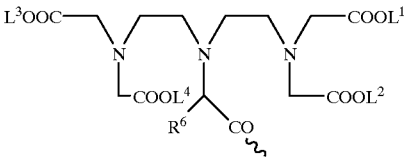

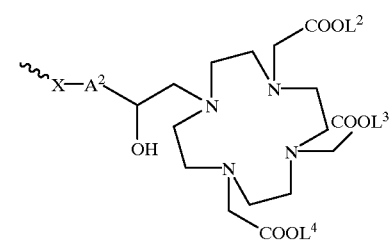

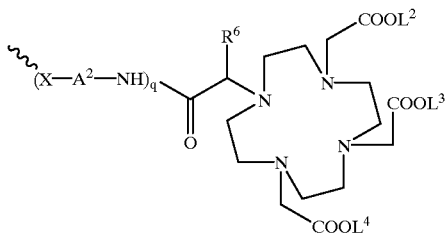

q is 0 or 1, $A^2$ is phenylene, —CH$_2$—NHCO—CH$_2$—CH(CH$_2$COOH)—C$_6$H$_4$, phenylenoxy, or $C_1$–$C_{12}$ or $C_7$–$C_{12}$ alkylene group that is optionally interrupted by one or more oxygen atoms, 1 to 3 —NHCO groups, 1 to 3 —CONH groups and/or substituted with 1 to 3 —(CH$_2$)$_{0-5}$ COOH groups, X is —CO or —NHCS, $R^6$ is a hydrogen atom, straight-chain or branched $C_1$–$C_7$ alkyl, phenyl or benzyl, and $L^1$, $L^2$, $L^3$ and $L^4$ are each, independently of one another, a hydrogen atom or a metal ion equivalent of an element of atomic numbers 20–32, 37–39, 42–51, or 57–83, provided that at least two of $L^1$, $L^2$, $L^3$ and $L^4$ stand for said metal ion equivalents and that other anions are present to compensate for optionally present charges in the metalloporphyrin, and in which free carboxylic acid groups that are not required for complexing are optionally present, in each case, as salts with physiologically compatible inorganic cations, as salts with physiologically compatible organic cations, as esters, or as amides.

2. A compound according to claim 1, wherein M is a $Zn^{2+}$, $In^{3+}$, $Cd^{2+}$, $Lu^{3+}$, $La^{3+}$, $Sn^{2+}$, $Sn^{4+}$, $Cd^{2+}$, $Mg^{2+}$, $Al^{3+}$, $B^{3+}$ or $Ga^{3+}$ ion.

3. A compound according to claim 1 wherein $R^1$ is —CH$_2$CH$_2$CH$_2$OH or —CH$_2$CH$_2$OH.

4. A compound according to claim 1, wherein $R^2$ and $R^3$ are the same.

5. A compound according to claim 1, wherein $R^2$ and $R^3$ are each ethyl.

6. A compound according to claim 1, wherein $R^4$ is methyl.

7. A compound according to claim 1, wherein $A^2$ is —CH$_2$—, —(CH$_2$)$_2$—, —CH$_2$OC$_6$H$_4$-β, —CH$_2$OCH$_2$—, —C$_6$H$_4$—, or —CH$_2$—NHCO—CH$_2$—CH(CH$_2$COOH)—C$_6$H$_4$-β group, and β stands for the binding site to X.

8. A compound according to claim 1, wherein X is CO.

9. A compound according to claim 1, wherein $R^6$ is a hydrogen atom or methyl.

10. A compound according to claim 1, wherein two or three of $L^1$, $L^2$, $L^3$ and $L^4$ are metal ion equivalents of chromium(III), manganese(II), manganese(III), iron(III), cobalt(II), cobalt(III), nickel(II), copper(II), praseodymium (II), neodymium(III), samarium(III) or ytterbium(III).

11. A compound according to claim 1, wherein at least two of $L^1$, $L^2$, $L^3$ and $L^4$ are metal ion equivalents of manganese (II), cobalt (II), nickel (II), copper (II) or praseodymium (II).

12. A compound according to claim 1, wherein three of $L^1$, $L^2$, $L^3$ and $L^4$ are chromium (III), manganese (III), iron (III), cobalt (III), neodymium (III), samarium (III) or ytterbium (III).

13. A compound according to claim 1, wherein two or three or substituent $L^1$, $L^2$, $L^3$ and $L^4$ are metal ion equivalents of gadolinium(III), dysprosium(III), manganese(II) and iron(III).

14. A compound according to claim 1, wherein M is a $Lu^{3+}$ or $Zn^{2+}$ ion.

15. A compound according to claim 1, wherein said compound is:

Lu$^{3+}$ complex of N,N'-{[9,10-diethyl-5,14-bis(3-hydroxypropyl)-4,15 dimethyl-8,11-imino-3,6:16,13 dinitrilo-1,18-benzodiazacyclo-eicosine-20,21-diyl]-bis[({[oxy-(1-oxo-propane-3,1-diyl)-imino]-ethane-2,1-diyl}-oxy)-ethane-2,1-diyl]}-diamide of [(3,6,9-tricarboxylato-3,6,9-triazaundecane-1,11-dioic acid-11-oyl), gadolinium complex, sodium salt], dichloride;

Lu$^{3+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis[({[oxy-(1-oxo-propane-3,1-diyl)-imino]-ethane-2, 1-diyl}-oxy)-ethane-2,1-diyl]}-diamide of [1,4,7,10-tetraazacyclododecane-1,4,7-tris(carboxylatomethyl)-10-(4-aza-3-oxo-nonan-2-yl-6-oyl)-gadolinium complex], dichloride;

Zn$^{2+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis[({[oxy-(1-oxo-propane-3,1-diyl)-imino]-ethane-2, 1-diyl}-oxy)-ethane-2,1-diyl]}-diamide of [(3,6,9-tricarboxylato-3,6,9,-triazaundecane-1,11 dioic acid-11-oyl, gadolinium complex, sodium salt], chloride;

Zn$^{2+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis[{[oxy-(1-oxo-propane-3,1-diyl)-imino]-ethane-2, 1-diyl}-oxy)-ethane-2,1-diyl]}-diamide of [1,4,7,10-tetraazacyclododecane-1,4,7-tris(carboxylatomethyl)-10-(4-aza-3-oxo-nona-2-yl-6-oyl), gadolinium complex], chloride;

Lu$^{3+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis{[oxy-(1-oxo-propane-3,1-diyl)-imino]-ethane-2,1-diyl}-diamide of [(3,6,9-tricarboxylatoo-3,6,9-triazaundecane-1,11-dioic acid-11-oyl), gadolinium complex, disodium salt], dichloride;

Lu$^{3+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis{[oxy-(1-oxo-propane-3,1-diyl)-imino]-ethane-2,1-diyl}-diamide of {1,4,7,10-tetraazacyclododecane-1,4,7-tris(carboxylatomethyl)-10-(4-aza-3-oxo-nonan-2-yl-6-oyl), gadolinium complex}, dichloride;

Zn$^{2+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis{[oxy-(1-oxo-propane-3,1-diyl)-imino]-ethane-2,1-diyl}-diamide of the [(3,6,9-tricarboxylato-3,6,9-triazaundecane-1,11 dioic acid-11-oyl), gadolinium complex, sodium salt], chloride;

Zn$^{2+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl}-bis{[oxy-(1-oxo-propane-3,1-diyl)-imino]-ethane-2,1-diyl}-diamide of [1,4,7,10-tetraazacyclododecane-1,4,7-tris(carboxylatomethyl)-10-(4-aza-3-oxo-nonan-2-yl-6-oyl), gadolinium complex], chloride;

Lu$^{3+}$ complex of {[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis[({[oxy-(ethane-2,1-diyl)-oxy]-ethane-2,1-diyl}-oxy)-ethane-2,1-diyl]}-diamide of [(3,6,9-tricarboxylato-3,6,9-triazaundecane-1,11-dioic acid-11-oyl), gadolinium complex, disodium salt], dichloride;

Lu$^{3+}$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl]-bis[({[oxy-(ethane-2,1-diyl)-oxy]-ethane-2,1-diyl}-oxy)-ethane-2,1-diyl]}-diamide of [1,4,7,10-tetraazacyclododecane-1,4,7-tris(carboxylatomethyl)-10-(4-aza-3-oxo-nonan-2-yl-6-oyl), gadolinium complex], dichloride;

Zn$^{2+}$ complex of N,N'-{[9,10-diethyl-5,14-bis(3-hydroxypropyl)-4,15-dimethyl-8,11-imino-3,6:16,13-dinitrilo-1,18-benzodiazacyclo-eicosine-20,21-diyl]-bis[{[oxy-(ethane-2,1-diyl)-oxy]-ethane-2,1-diyl}-oxy)-ethane-2,1-diyl]}-diamide of [(3,6,9-tricarboxylato-3,6,9-triazaundecane-1,11 dioic acid-11-oyl), gadolinium complex, sodium salt], chloride; or Zn$^2$ complex of N,N'-{[9,10-diethyl-5,14-bis(3-hydroxypropyl)-4,15-dimethyl-8,11-imino-3,6:16,13 dinitrilo-1,18-benzodiazacyclo-eicosine-20,21-diyl-bis[({[oxy-(ethane-2,1-diyl)-oxy]-ethane-2,1-diyl}-oxy)-ethane-2,1-diyl]}-diamide of [1,4,7,10-tetraazacyclododecane-1,4,7-tris(carboxylatomethyl)-10-(4-aza-3-oxo-nona-2-yl-6-oyl)-gadolinium complex], chloride.

16. A method of performing photodynamic therapy on a patient comprising administering a photodynamic agent to said patient and irradiating said agent, wherein said agent is a complex compound according to claim 1.

17. A method of MRI diagnostic monitoring of photodynamic therapy comprising administering to a patient a photodynamic agent which is paramagnetic, irradiating said agent, and monitoring the photodynamic therapy induced thereby using magnetic resonance imaging, wherein said agent is a complex compound according to claim 1.

18. A method according to claim 16, wherein said agent is administered in the amount of 0.01 $\mu$mol–2 mmol/kg of bodyweight.

19. A method according to claim 17, wherein said agent is administered in the amount of 0.01 $\mu$mol–2 mmol/kg of bodyweight.

20. A pharmaceutical composition comprising: a complex compound according to claim 1, suspended or dissolve in an aqueous medium, and optionally at least one galenical additive.

21. A composition according to claim 20, the said composition contains a physiologically harmless buffer, a complexing agent, an electrolyte, an antioxidant, or a combination thereof.

* * * * *